United States Patent [19]

Erickson

[11] Patent Number: 5,249,163
[45] Date of Patent: Sep. 28, 1993

[54] OPTICAL LEVER FOR ACOUSTIC AND ULTRASOUND SENSOR

[76] Inventor: Jon W. Erickson, 3406 Rambow Dr., Palo Alto, Calif. 94306

[21] Appl. No.: 895,544

[22] Filed: Jun. 8, 1992

[51] Int. Cl.⁵ .............................................. G01H 1/00
[52] U.S. Cl. .................................. 367/149; 367/151; 73/653; 73/655; 359/212; 359/214
[58] Field of Search ...................... 367/140, 149, 151; 73/653, 655; 359/212, 214

[56] References Cited

U.S. PATENT DOCUMENTS

| | | | |
|---|---|---|---|
| 3,364,813 | 1/1968 | McKinney | 73/655 |
| 3,831,137 | 8/1974 | Cuomo | 73/653 |
| 3,998,092 | 12/1976 | Maccabee | 73/655 |
| 4,185,503 | 1/1980 | Saito | 73/653 |
| 4,310,905 | 1/1982 | Palmer | 367/140 |
| 4,482,805 | 11/1984 | Palmer | 367/140 |
| 5,063,781 | 11/1991 | Conforti et al. | 73/653 |

Primary Examiner—J. Woodrow Eldred
Attorney, Agent, or Firm—James J. Leary

[57] ABSTRACT

An acoustic sensor, suitable for use as an ultrasonic transducer, microphone or hydrophone, uses an optical lever to amplify the motion of the sensor surface and convert it to an electrical signal suitable for image processing. In the acoustic sensor, a beam of light from a laser is directed at an oblique angle onto a reflective surface coupled to a sensor membrane. The reflected light strikes a position-sensitive light detector (PSD) which generates an electrical signal indicative of the position of the spot of light on the PSD. When an incident acoustic wave strikes the sensor membrane, the small movements of the reflective surface result in large motions of the spot of light on the PSD, thereby amplifying the acoustic signal and converting it into an electrical signal. Also disclosed is a multi-element sensor array suitable for linear array or phased array imaging.

16 Claims, 5 Drawing Sheets

Cross-sectional view of a solid membrane sensor

Cross-sectional view of a polymer membrane sensor

Cross-sectional view of sensor with cantilever

OPTICAL LEVER FOR ACOUSTIC AND ULTRASOUND SENSOR

FIELD OF THE INVENTION

The present invention relates generally to diagnostic medical instrumentation and, more particularly, to ultrasonic transducers used in medical imaging. A primary objective of the present invention is to provide a robust, low-cost transducer with increased sensitivity to ultrasound signals.

BACKGROUND OF THE INVENTION

A typical ultrasonic imaging system makes use of one or more piezoelectric transducers which act as the source (actuator) of the ultrasonic beam or signal, and which often also serve to sense the reflected signal (sensor). An electrical pulse generated by an electronic control module is converted to an ultrasonic pulse by the transducer/actuator in the probe. The probe is in contact with the body, and the ultrasonic pulse is transmitted therein. The pulse is then absorbed by body tissues or reflected to different degrees from the boundaries between body tissues. The reflections reach the transducer/sensor at different times, which vary with the distance to the tissue boundaries. The reflections also have different energies, due the different acoustic impedances of the tissues, as well as absorption by the intervening tissues. The transducer/sensor converts the reflections into a weak electrical signal, which contains information that can be processed into an image of the body.

A great variety of ultrasonic transducers are presently in use or under development. Shapes and sizes vary widely in order to meet special needs. Focusing by electronic or mechanical means, or some combination thereof, can be used to produce and steer a narrow ultrasonic beam of desired focal length. Likewise, mechanical and electronic focusing can be used to sense the reflections from a particular direction and distance. Phased transducer arrays of various configurations have been employed to achieve particular focusing properties, under electronic control. (The term "phased array" is taken from radar technology, in which the phase relationships of signals from multiple antennae are processed electronically to improve resolution and sensitivity.) The acquired signal is then converted into an image using analog or, depending on cost and technological considerations, digital processing.

Good resolution of ultrasound images is important for medical applications. Some limits to resolution are fundamental to the physics of wave propagation (for example, acoustic shadows and reverberations, and geometric artifacts) and are best dealt with by educating the user, or by appropriate image processing algorithms. Other factors affecting resolution involve transducers and electronic instrumentation (such as axial and lateral resolution, and dynamic range) and are susceptible to improvement.

Axial resolution can be limited in part by the wavelength of the ultrasonic signal ("ultrasound" simply designates sound waves of a frequency above the audible range, with wavelengths of millimeters or less). Absorption of ultrasonic energy by body tissues tends to restrict the useful depth of field to about 200 wavelengths, due to attenuation of the signal. Thus resolution can be improved by use of shorter wavelengths (higher frequencies) but this also implies a shallower depth of field.

For a simple system with a single element and spherical or parabolic focusing, the lateral resolution is limited by the aperture of the transducer. Larger apertures provide greater resolution but shallower depth of field. The size of the transducer element or elements also can limit the resolution, since the detected signal will be known to originate from a given transducer but not any particular location on that transducer.

The dynamic range of the instrument determines the useful number of gray scale levels in the image. Most commercial transducers use piezoelectric crystal elements or other materials (e.g. plastics or polymers) both as actuators which produce the ultrasonic pulse, and as sensors which detect the reflected signal. The physics and engineering of piezoelectric sensors are relatively well understood. The sensitivity of a simple piezoelectric sensor, such as a small block of quartz, can be greatly improved by use of a more complicated geometry, the "piezoelectric bimorph" shape. The bimorph has been used since 1930 in microphones and phonograph needle assemblies, but various design considerations such as high cost and fragility preclude its use in ultrasound transducers.

An alternative means of sensing small deflections or increments of motion is the optical lever. Optical levers have proven to be effective in routine measurements of extremely small deflections, of less than 0.01 nanometer, in atomic force microscopy (AFM). This measurement strategy can be implemented in robust ultrasound transducers at low cost, with great flexibility in design.

SUMMARY OF THE INVENTION

In distinct contrast to the piezoelectric transducer/-sensors of the prior art, the present invention proposes the use of an optical lever to detect the ultrasonic reflections. The optical lever makes use of a beam of light shining at an oblique angle on a mirrored surface (e.g., a membrane or piston) in good acoustic contact with the ultrasonic medium. The reflected beam of light is directed onto a position-sensitive detector. Small movements in the mirrored surface result in relatively large changes in the position where the beam of light strikes the detector. The position-sensitive detector is insensitive to fluctuations in the light intensity, which lowers the overall costs (especially in arrays of such sensors). The size of the sensor and of the transducer as a whole can also be reduced considerably, since all the components can be fabricated with microelectronic techniques.

DESCRIPTION OF THE PREFERRED EMBODIMENTS

Figure 1:
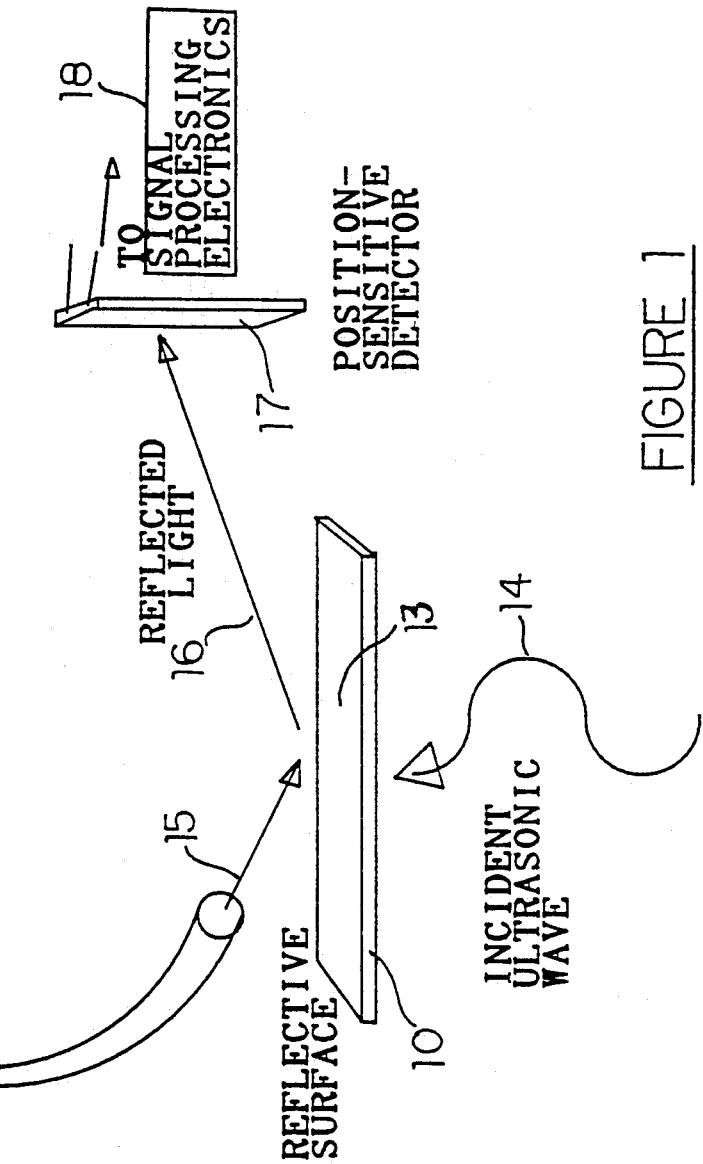
FIG. 1 shows a perspective schematic of the optical lever ultrasound sensor.

FIG. 1 shows a schematic view of an optical lever ultrasound sensor built in accordance with the present invention. A light source 11 is used to generate a narrow beam of collimated light 15 which is directed toward a reflective surface 13 at an acute angle to the surface. In the preferred embodiment, the light source 11 is a laser light source and a single mode optical fiber 12 directs the beam of light 15 onto the reflective surface 13. Alternatively, a source of collimated light other than a laser may be coupled to the optical fiber 12, or a laser light source, for instance an integrated AlGaAs/GaAs diode laser, may be used to direct a beam of light 15 directly onto the reflective surface 13 without the use of an optical fiber 12.

The reflected light beam 16 from the reflective surface 13 strikes a position-sensitive light detector (PSD) 17, which generates a signal indicative of the position at which the beam of light 16 strikes the PSD 17. The reflective surface 13 is coupled to a membrane 10 which moves in reaction to an incident ultrasonic wave 14. When the membrane 10 is at rest, the reflected light beam 16 strikes somewhere near the center of the PSD 17. The small movements of the reflective surface 13 due to the incoming ultrasonic wave 14, result in large movements of the position at which the reflected light 16 strikes the PSD 17. The PSD 17 is sensitive to movements of greater than 5 nm in the location of the spot of light on it. The deflection of the reflective surface 13 is thus amplified by this optical lever, the amplification being determined by the distance of the PSD 17 from the reflective sensor surface 13.

The output of the PSD 17 is a voltage signal which varies in proportion to the position of the light spot on the PSD surface, which in turn is proportional to the amplitude of the vibrations of the reflective sensor surface 13, and to the amplitude of the ultrasonic pressure wave 14. The signal has a very low level of noise due to the measurement process or strategy.

The PSD 17 output is processed by the imaging electronics 18, either as a single element or as one channel of an array of sensors. The leading edge of the incident pulse may be used in such an array to electronically focus on the position of the echo source. This positional information is then used to build up an image of the objects or tissue interfaces responsible for the echoes.

Figure 2:
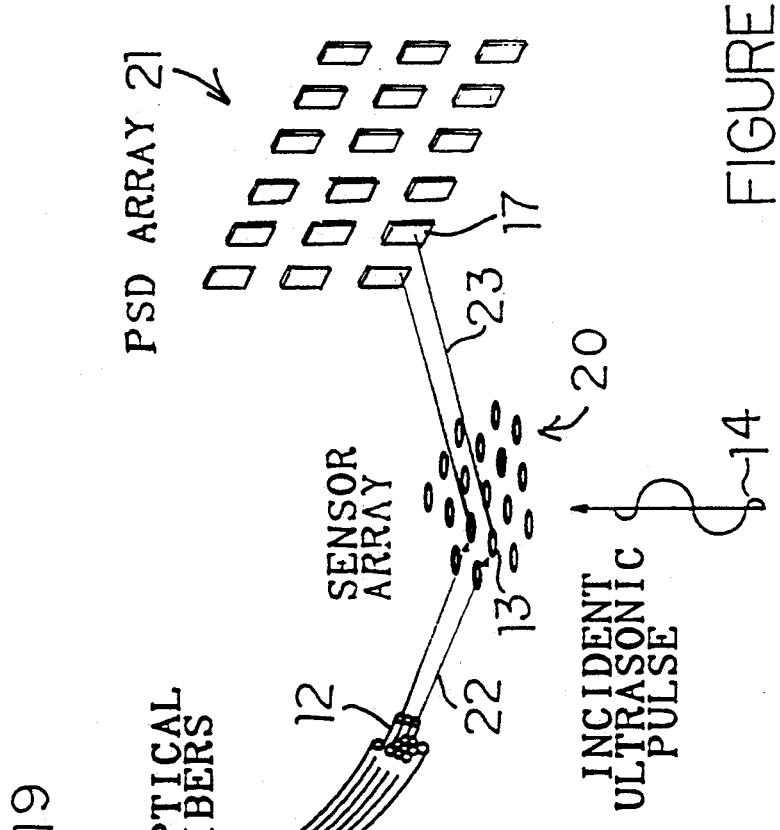
FIG. 2 shows a perspective schematic of a sensor array using the optical lever ultrasound sensor.

FIG. 2 shows one manner of constructing an array of ultrasound sensors using the principle of the optical lever. A light source 11, preferably a laser light source, generates a collimated beam of light which is coupled to a bundle of optical fibers 19. Each of the optical fibers 12 within the bundle 19 directs a narrow beam of light 22 onto one of the reflective sensor elements 13 within an array of sensors 20. Each beam of reflected light 23 strikes one of the PSD elements 17 within a PSD array 21. The PSD array 21 may be made from a number of separate PSD elements 17, or a large scale integrated array of detectors may be manufactured on a single chip.

Each set of one optical fiber 12, one reflective sensor element 13 and one PSD element 17 is analogous to the single sensor shown in FIG. 1. Thus a number of sensors can be integrated together to form a linear array, a square array or other desired geometries of sensor arrays.

Figure 3:
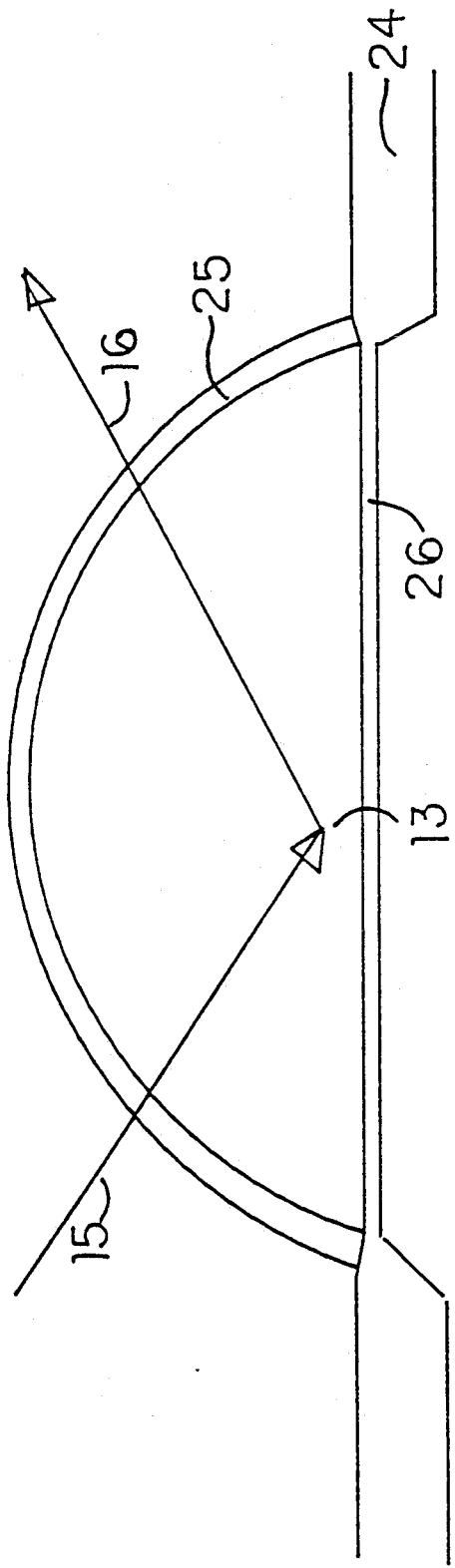
FIG. 3 shows a cutaway perspective of an ultrasound sensor element having a solid reflective membrane.

FIG. 3 shows one preferred embodiment for the reflective sensor elements for a single ultrasound sensor or an array of ultrasound sensors. A substrate 24, which may be a metal, ceramic, polymer or other material, is etched or machined to form a thin membrane 26. The extent of the membrane 26 determines the aperture 25 of the sensor. A reflective surface 13 is coupled to the back of the membrane 26. The reflective surface 13 may be simply the polished rear surface of the membrane 26, or the membrane 26 may be metalized to provide a reflective surface 13.

The material of the substrate 24 and the membrane 26 may be chosen so that it has the proper combination of density and stiffness to match the acoustic impedance of the acoustic medium to be imaged. Alternately, other well known techniques, such as quarter wave matching layers, can be used to provide good acoustic coupling. The space behind the membrane 26 may be filed with a damping material to prevent excessive ringing of the sensor.

Figure 4:
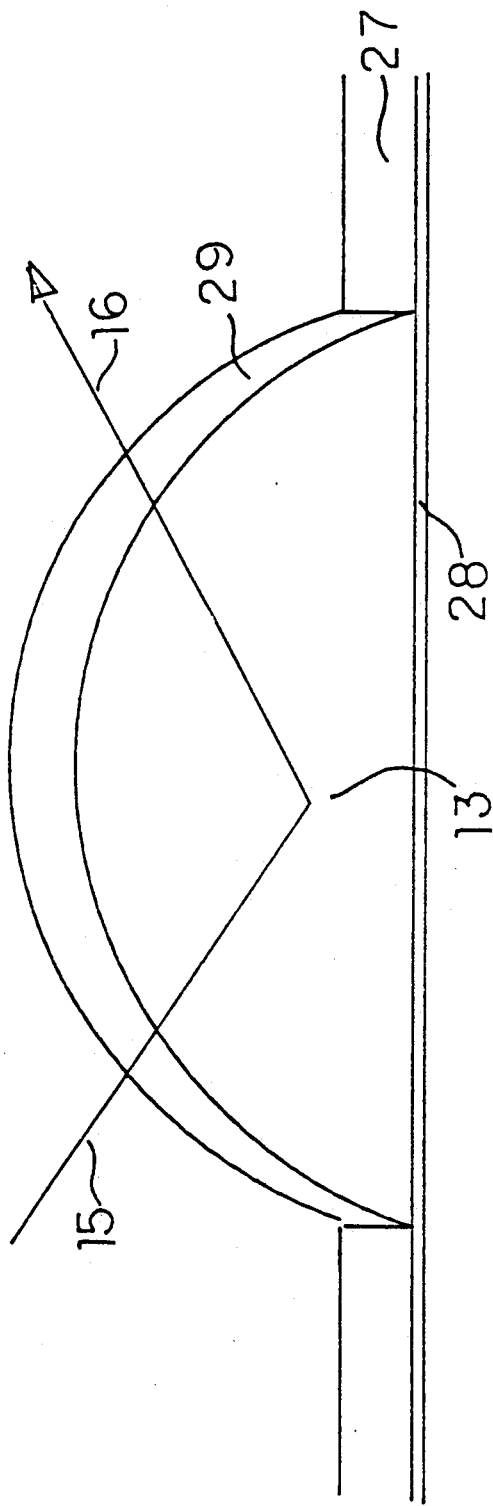
FIG. 4 shows a cutaway perspective of an ultrasound sensor element having a polymer reflective membrane.

FIG. 4 shows another preferred embodiment of the reflective sensor element. An aperture 29 is formed in a substrate 27 by etching, machining or other methods. A membrane 28, which is a thin layer of metal, polymer or other material, is placed over the aperture 29. A reflective surface 13 is formed on the back of the membrane 28, for instance, by polishing or metalization. The material of the membrane 28 may be chosen to match the acoustic impedance of the imaging medium. An advantage of this design is that the substrate material 27 may be chosen solely for its structural properties since it does not need to have the same acoustic properties as the membrane 28. Again a damping material may be added to prevent excessive ringing in the sensor.

Figure 5:
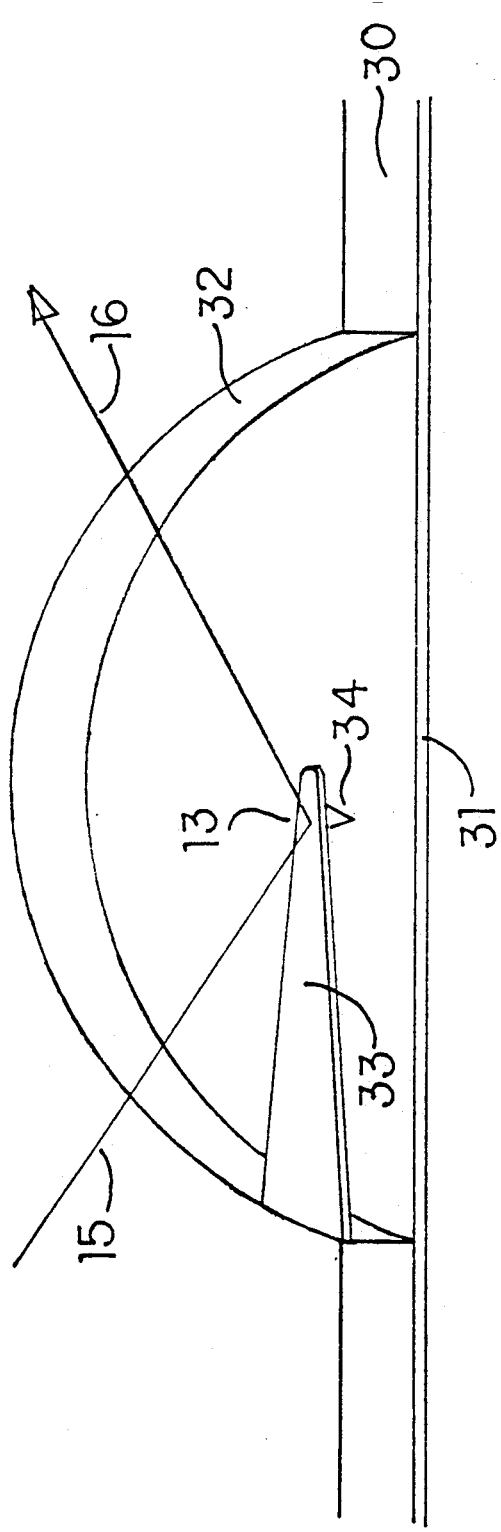
FIG. 5 shows a cutaway perspective of an ultrasound sensor element having a cantilever with a light reflective surface.

FIG. 5 shows a third preferred embodiment of the reflective sensor element that combines a membrane 31 with a cantilever 33. An aperture 32 is formed in a substrate 30. A cantilever 33 mounted on the substrate 30 contacts the membrane 31 near the middle of the aperture 32 by means of a stylus 34 or other coupling link. A reflective surface 13 is formed on the back of the cantilever 33.

In this design, the acoustic impedance of the sensor is determined by the combined mass of the cantilever and the membrane, and the combined stiffness of the cantilever and the membrane. This allows additional flexibility in the design of the sensor for matching impedance and for tuning the sensitivity of the sensor. The cantilever can also be used to linearize the pressure response of the sensor. If the response of the membrane sensor by itself does not obey Hooke's law, a cantilever with the desired force constant may be added to improve the sensor's linearity.

TECHNICAL DISCUSSION

Sensitivity

A typical piezoelectric sensor may have a sensitivity, measured in units of power per area, on the order of $10^{-7}$ Watt $cm^{-2}$. When operating at a recommended biological threshold limit of about $10^{-2}$ Watt $cm^{-2}$, signal attenuation due to absorption by biological tissue limits the depth of view to about 200 wavelengths. For a 3 MHz signal, a 10 cm depth corresponds to a loss of about 5 orders of magnitude in signal strength.

In contrast, an optical lever sensor can detect signals of less than $10^{-18}$ Watt $cm^{-2}$. (This corresponds to a routine situation in AFM involving a deflection of 0.01 nm against a force constant of 2 Newton m$^{-1}$, measured in less than 10$^{-3}$ second.) Thus an initial signal of 10$^{-2}$ Watt cm$^{-2}$ may in theory be attenuated by 16 orders of magnitude.

The increased sensitivity (with respect to conventional piezoelectric transducers) can be used in several different ways. The size of the sensor may be reduced, which may have advantages in terms of image resolution (both axial and lateral). The dynamic range of the acquired signal may be increased, which can be used to improve image quality. The power of the initial signal may be decreased, which may be a consideration for examination of certain kinds of biological tissue (e.g. eyes, embryos). Shorter wavelengths of ultrasound may be used while still viewing depths of at least 10 cm, which would improve axial resolution.

Dynamic Range

In practice, it is convenient to limit the dynamic range to 12 orders of magnitude or less. The practical constraints on dynamic range are the amplitude of the deflection produced by the ultrasound excitation of the membrane, diaphragm, or piston; and the size of the position-sensitive detector (PSD). A nearly linear response of the vibrating surface to the excitation is desirable, and this will constrain the acceptable amplitude.

Should larger amplitudes be acceptable for the vibrating surface in a given implementation, it may be useful to adjust the sensitivity. Range switching is accomplished relatively easily, by shortening the lever arm, or moving the PSD closer to the point of reflection. A typical commercially available PSD is about 5 mm in length and can distinguish positions of incident light that are separated by more than about 5 nm. This gives a dynamic range of about 6 orders of magnitude in amplitude, or about 12 orders of magnitude in intensity. If the distance to the point of reflection is shortened by a factor of 100, the sensitivity will be less, but signals 100 times larger in amplitude (or 10,000 in intensity) may be measured.

Resolution

When a sensor is smaller in size than the wavelength of the detected signal, the phase of the signal becomes an important parameter in determining the resolution. Pulsewidth or the duration of the excitation may be of less concern. For example, the small size and great sensitivity of the sensor can be used to detect the phase of the wave and identify the leading edge, rather than the entire pulse. If the arriving edge detection is very efficient, the axial resolution may be limited by the lateral solid angle subtended by the sensor.

Lateral resolution also may be enhanced by the small size of the sensor. Most present designs do not detect where on a given sensor element the incident ultrasound wave impinges. Therefore, the lateral resolution is limited not only by the distance between sensor elements, but by the size of each element.

Thermal and Other Noise

Thermal and other energy fluctuations will provide a background of vibrations in the ultrasound frequency range, for which the probability can be readily estimated. Well known techniques exist for addressing this problem, such as moving the signal to a part of the frequency domain which is lower in noise, or the use of a lock-in amplifier.

Linear and Square Arrays

This measurement strategy lends itself to high-yield, low-cost manufacture. In most implementations a separate actuator and sensor is required, instead of the single transducer. However, the low cost should compensate for the separation of functions. Moreover, the separation of functions itself should permit the use of cheaper materials that need not serve both as actuator and sensor.

The sensor elements can be scaled over a wide range of sizes. Arrays of such elements can be used in electronic focusing. Generally linear arrays have proved adequate in medical imaging, since two dimensions suffice for most present diagnostic purposes. Square or two-dimensional arrays are also possible, giving rise to the possibility of three-dimensional ultrasonic imaging.

The Reflective Surface

The reflective surface must be in contact with the ultrasonic medium, and should be displaced similarly by waves of similar amplitude. The simplest response function is linear. For example, the surface response will obey Hooke's law (F=kx) if the force opposing displacement is proportional to the magnitude of the displacement. The displacement due to the incident ultrasonic wave or pulse must also be quickly damped, in order to avoid subsequent ringing or spurious signal.

A stable force constant can be achieved in various implementations. Examples include silicon or polymer membranes or diaphragms, solid or fluid pistons, and micromachined springs or cantilevers.

Membranes or diaphragms designate thin, usually circular and planar bodies fastened at the periphery to a thicker support. Often the material itself opposes motion out of the plane of the resting surface, although another force constant may be imposed (e.g. the cantilever in FIG. 5). An air-fluid interface by itself provides a simple reflective surface in which surface tension opposes displacement, but also presents many design problems incompatible with a wide variety of sensor applications. Membranes and diaphragms made of solids such as silicon, or polymers of various kinds, are, however, the preferred choice in most applications.

Pistons designate either solids or fluids (liquids or gases) which move along the axis of a cylindrical cavity in response to the ultrasonic wave. Problems of friction would seem to be more readily overcome with fluid pistons, such as ferromagnetic liquids. The movement of the piston is typically opposed by a force proportional to the displacement, for example due to compression of a solid spring or a volume of gas.

The above examples serve simply to illustrate ways to design or fabricate a reflective surface with a reproducible and sensitive response to ultrasonic excitation.

CONCLUSION, RAMIFICATIONS, AND SCOPE

The present invention provides for many alternatives to the embodiments described above.

Both analog and digital signal processing can be used with virtually no changes from current imaging technology. This allows full use of the great art and ingenuity presently achieved in ultrasound signal processing, to deliver the maximum diagnostic value in medical care.

Sensitivity

Very low noise (proven by AFM) is integral to the design. The optical lever in effect acts as an amplifier with a high gain and low noise.

Resolution

High axial resolution is possible, perhaps even with longer wavelengths of ultrasound. Sensor elements smaller than the wavelength could be used, which should permit reliable measurement of phase.

Similarly small sensor elements could aid in improving lateral resolution, by increasing the precision with which the signal coordinates are determined.

Robust

Optical levers have already proven to be a robust measurement strategy.

Low Cost

The cost is low, and suitable for arrays and wide range of designs (e.g. catheter or invasive as well as non-invasive sensing). A single laser source could be used for an entire array of sensors, with a suitable number of optical fibers.

The ultrasound source or transducer/actuator can be made up of less expensive piezoelectric materials, since these do not need to play a dual role as transducer/sensors as well.

Suited to Miniaturization and Mass-Production

The sensor design is well-suited for planar microfabrication technology like that used in integrated circuits and increasingly in micromechanical sensors and actuators.

Low-Power

The sensor design requires only low power levels and thus is well-suited to use in portable ultrasound units. The great sensitivity of the sensor requires less power in the ultrasound source as well.

The power needed to drive the ultrasound source or transducer/actuators can be reduced, due to the sensitivity of the transducer/sensors.

Dynamic Range

The greater sensitivity and lower noise of the design confer an increased dynamic range. This can be used to deliver better image clarity, with its attendant clinical diagnostic values.

Other Applications

Though specifically conceived for use as an ultrasound transducer, the optical lever acoustic sensor of the present invention is also suitable for use as a microphone or hydrophone in the ultrasonic or audible range. With proper calibration, the present invention would also be useful as a pressure transducer for measurement of static or dynamic fluid pressure.

While the foregoing description contains many specific details, these should not be construed as limitations on the scope of the invention, but rather as an exemplification of some of its preferred embodiments. Many other variations are possible and will no doubt occur to others upon reading and understanding the preceding description. Accordingly, the scope of the invention should be determined, not by the embodiment illustrated, but by the appended claims and their legal equivalents.

I claim:

1. A sonic transducer comprising:
   a reflective surface responsive to incident sound waves,
   a light beam incident upon said reflective surface,
   a reflected light beam which is the reflection of said incident light beam from said reflective surface,
   a position sensitive light detector so arranged as to sense the position of said reflected light beam, said position sensitive light detector being sensitive to the position of said reflected light beam on said light detector and said position sensitive light detector being insensitive to changes in the intensity of said reflected light beam.

2. The sonic transducer of claim 1 wherein said incident light beam is incident upon said reflective surface at an acute angle, and wherein the position of said reflected light beam is indicative of the position of said reflective surface.

3. The sonic transducer of claim 2 wherein the motion of said reflected light beam at said position sensitive light detector is greater than the motion of said reflective surface, thereby serving to amplify the motion of said reflective surface.

4. The sonic transducer of claim 1 wherein said reflective surface comprises a membrane responsive to incident sound waves.

5. The sonic transducer of claim 4 wherein said membrane is formed of a polymer material.

6. The sonic transducer of claim 1 wherein said reflective surface comprises a cantilever which is responsive to incident sound waves.

7. The sonic transducer of claim 6 wherein said cantilever is responsive to the motion of a membrane which is responsive to incident sound waves.

8. The sonic transducer of claim 1 further comprising a light source for producing said incident light beam.

9. The sonic transducer of claim 8 further comprising an optical fiber for directing said incident light beam from said light source onto said reflective surface.

10. The sonic transducer of claim 8 wherein said light source comprises a laser light source.

11. The sonic transducer of claim 10 further comprising an optical fiber for directing said incident light beam from said laser light source onto said reflective surface.

12. A sonic transducer array comprising:
    a plurality of reflective surfaces, each independently responsive to incident sound waves,
    at least one light beam incident upon said reflective surfaces,
    a plurality of reflected light beams which are the reflection of said at least one incident light beam from said reflective surfaces,
    a plurality of position sensitive light detectors so arranged as to sense the positions of said reflected light beams, said position sensitive light detectors being sensitive to the position of said reflected light beams on said light detectors and said position sensitive light detectors being insensitive to changes in the intensity of said reflected light beams.

13. The sonic transducer of claim 12 comprising a plurality of incident light beams, each of said incident light beams being incident upon one of said plurality of reflective surfaces.

14. A method of detecting sound waves comprising the steps of:
directing an incoming beam of light onto a reflective surface responsive to incident sound waves,
detecting the position of a reflected light beam, which is the reflection of said incoming beam of light from said reflective surface,
converting the detected position of said reflected light beam into a signal indicative of the movement of said reflective surface in response to said incident sound waves.

15. The sonic transducer array of claim 12, wherein said at least one light beam comprises a single light beam which is incident on all of said plurality of reflective surfaces and said plurality of reflected light beams are the reflections of said single light beam off of said plurality of reflective surfaces.

16. The sonic transducer array of claim 12, wherein said at least one light beam comprises a plurality of light beams and each of said plurality of light beams is reflected off of each of said plurality of reflective surfaces to form said plurality of reflected light beams.

* * * * *